United States Patent [19]

Kraus

[11] Patent Number: 5,382,250
[45] Date of Patent: Jan. 17, 1995

[54] CRANIAL DRILL STOP

[75] Inventor: Robert Kraus, Attleboro, Mass.

[73] Assignee: Johnson & Johnson Professional Inc., Raynham, Mass.

[21] Appl. No.: 207,978

[22] Filed: Mar. 8, 1994

[51] Int. Cl.⁶ ............................................. A61B 17/16
[52] U.S. Cl. ................................. 606/80; 408/202; 606/172
[58] Field of Search ................. 606/172, 80, 79, 96, 606/97, 98, 130; 408/202, 241 S

[56] References Cited

U.S. PATENT DOCUMENTS

| | | | |
|---|---|---|---|
| 2,525,669 | 10/1950 | Hainault | 606/80 X |
| 3,017,643 | 1/1962 | Lehde, Jr. | 408/202 |
| 3,682,177 | 8/1972 | Ames et al. | 408/202 X |
| 4,039,266 | 8/1977 | O'Connell | 408/202 |
| 4,456,010 | 6/1984 | Reimels et al. | 606/80 X |
| 4,521,145 | 6/1985 | Bieler | 408/202 X |
| 4,931,056 | 6/1990 | Ghajar et al. | 606/130 |
| 5,080,535 | 1/1992 | Hirano | 408/202 X |
| 5,092,717 | 3/1992 | Fischer | 408/202 X |

Primary Examiner—Peter A. Aschenbrenner
Attorney, Agent, or Firm—Michael Q. Tatlow

[57] ABSTRACT

A device to stop the penetration of a cranial drill that is used to pierce the skull during neurosurgical procedures. The device uses a plurality of spacers that each have a body in the form of a cylinder having a bore extending therethrough with a flat disc adjacent the cylindrical body with a plurality of tabs fixed to the disk in a circumferential pattern around the bore and axially aligned therewith. The periphery of the disk having a diameter larger than the cylindrical body portion to form a gripping member. Each of the tabs having an indent positioned on an outer surface and an interior surface of the cylindrical body portion having a bead positioned around the interior diameter of the cylindrical body portion so that the indents in the tabs are adapted to engage and retain a bead of another spacer when the spacers are fitted together to define a drill stop. Each of the plurality of spacers are of different lengths than at least one of the other spacers.

2 Claims, 2 Drawing Sheets

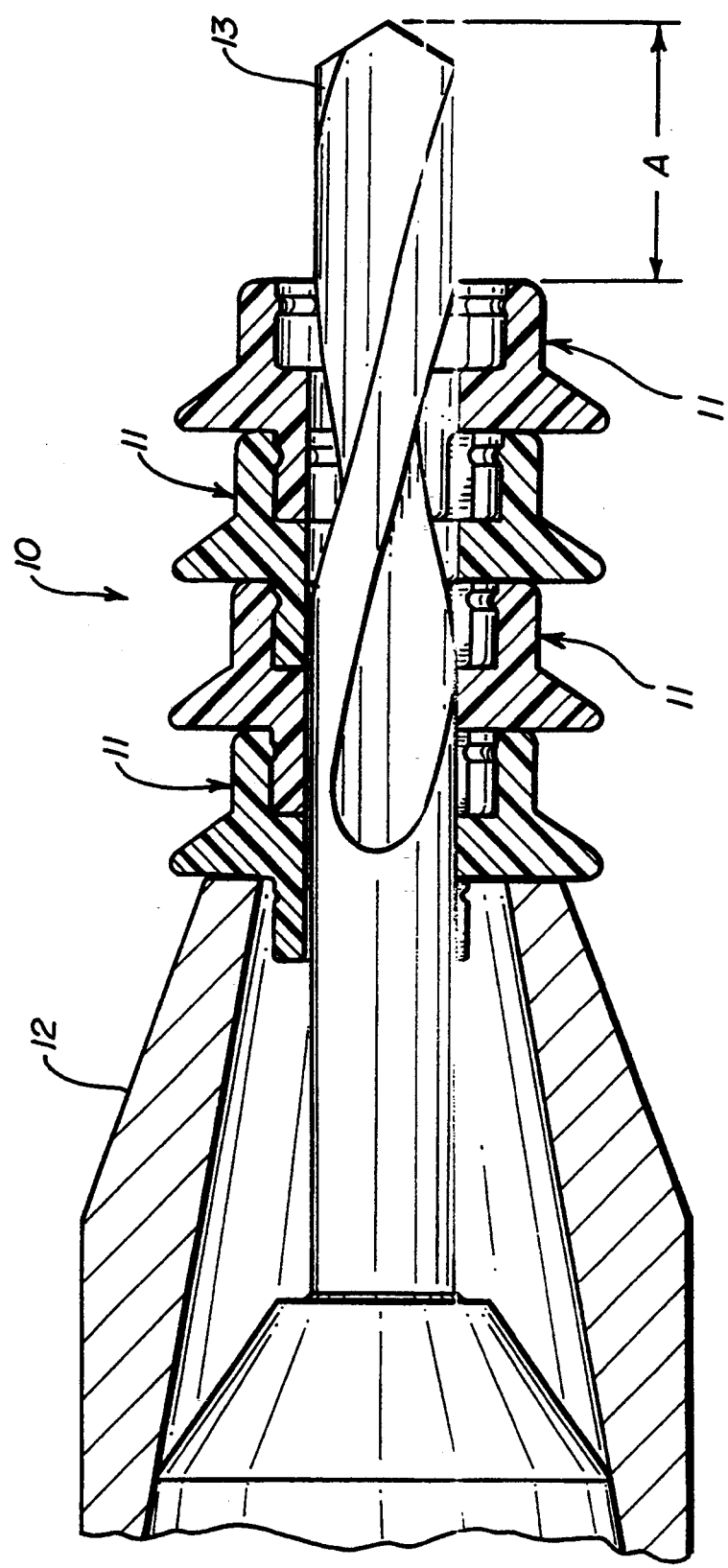

CRANIAL DRILL STOP

BACKGROUND OF THE INVENTION

The present invention relates to a device to stop the penetration of a cranial drill that is used to pierce the skull during neurosurgical procedures. Many neurosurgical procedures such as ventriculoscopy and ventriculography procedures require the piercing or opening of the patient's skull to perform the procedure or to insert devices which measure pressure or to provide drainage. In these procedures, the skull is perforated with a cranial perforator or with a cranial drill. Cranial drills are usually twist drill bits which are secured to a manual hand operated drill or a power drill, either an electric or pneumatic drill.

Care must be exercised in the utilization of twist drills in drilling openings in the skull to prevent the drill from extending through the skull into the dura.

Drill stops of different types have previously been used in performing cranial surgery. Typical of these adjustable guards or stops to control the depth of penetration of cranial drilling instruments is that shown in U.S. Pat. No. 3,682,177. This patent discloses a manually operated drill with a twist drill point and an adjustable depth guard surrounding the drill bit. The depth guard is held in position by a coupling and a set screw.

Another drill guide and stop mechanism are shown in Ghajar U.S. Pat. No. 4,931,056. This patent discloses a drill guide which is a platform with legs arranged in a triangle which positions the drill guide over the drill entry point on the skull. There is a tube affixed to the platform into which the drill bit is inserted to guide the drill into position. A series of spacer rings are affixed to the handle of the drill bit which control the depth of the drill guide. The spacer ring contacts the top of the guide tube to limit the penetration of the drill bit into the skull. The spacers can be either constructed as separate units or may be a single unit with perforated portions to break off to obtain the desired depth. The mechanism employed in the Ghajar drill is suitable only in connection with the base as the stops are not attached to the drill and are designed to butt against the top of the tubular drill guide which is affixed to the base of the device.

Another commonly employed drill stop is a circular bushing with a bore that is sized for the particular size drill bit. A set screw is used to lock the bushing to the drill bit and limit the effective drilling length and penetration of the drill bit.

SUMMARY OF THE PRESENT INVENTION

The present invention provides a drill stop for a cranial drill particularly of the twist type. The drill stop may be used with either hand cranked drills or with power drills of different types. The drill stop comprises a series of interlocking spacers which are held in place in a standardized drill chuck and interlock to expose only the desired length of the twist drill which is necessary to perform the particular surgical procedure. Each spacer is made to interlock with a similar spacer so that the desired number of spacers can be fitted around the drill bit to provide the correct exposure of the drill bit beyond the drill stop and therefore the correct penetration of the drill bit through the skull.

BRIEF DESCRIPTION OF THE DRAWINGS

FIG. 1 is a view, of the drill stop of the present invention in cross section around a drill bit.

DETAIL DESCRIPTION OF THE PRESENT INVENTION

Figure 3:
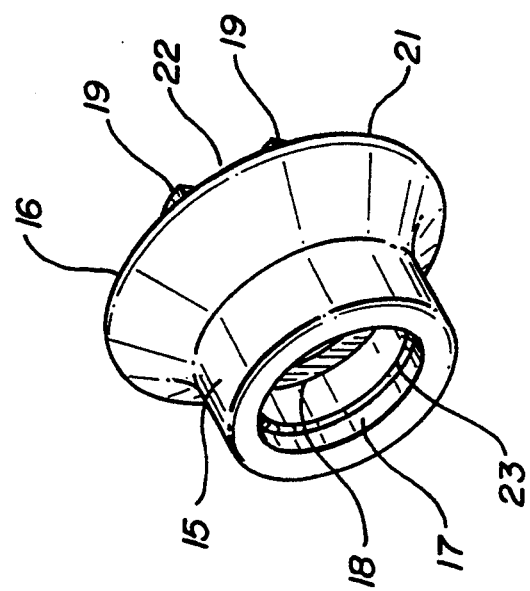
FIG. 3 and FIG. 4 are perspective views of a spacer of the present invention.

Turning to FIG. 1, the drill stop 10 of the present invention is made up of a series of individual spacers 11 which are interlocked together to form the desired length. There is a central opening 14 or bore formed by the stacked or combined spacers. The bore is sized so that the drill bit 13 can fit through the bore 14. A No. 1 drill bit commonly used in drill openings in the skull for ventriculostomy procedures has a diameter of 0.228 inch. The spacers are held in the chuck 12 which also holds the drill bit. Drill 13 extends beyond the distal spacer a distance indicated at A in the drawing. This is the distance that the drill bit will penetrate the skull or other surface. This distance can be adjusted by adding or removing individual spacers.

Figure 4:
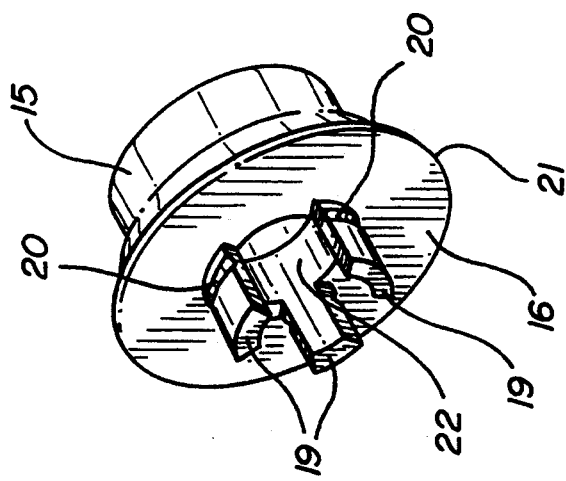
Figure 2:
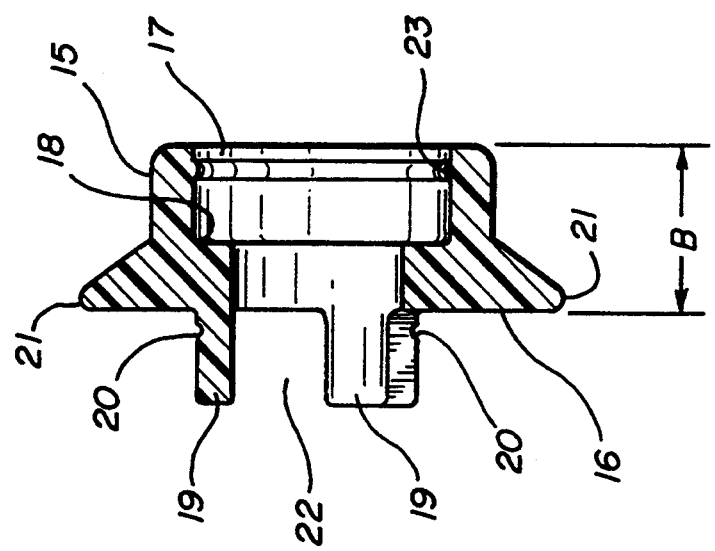
FIG. 2 shows a cross sectional view of one of the spacers of the present invention.

The construction of the individual spacers are shown in FIGS. 2, 3 and 4. Each individual spacer comprises a cylindrical portion 15 and a disc portion 16. There is a bore 17 through the cylindrical portion which ends on a shoulder 18. The disc portion 16 has at least three tabs 19 extending perpendicular from the face of the disc. The number of tabs on the spacer is equal to the number of jaws on the drill chuck of the drill to be used. If the drill chuck has four jaws, the spacer would have four tabs. These tabs 19 have an indent 20 on their periphery. The disc 16 ends in a flange 21 which can be used to grip the individual spacer when assembling or disassembling the spacers into the drill stop. The arrangement of the tabs 19 defines a bore 22 which is axially aligned with the bore 17 in the cylindrical portion of the spacer. The bore 22 is sized to correspond to a particular size drill bit. That is, the bore 22 would be one quarter inch for use with a one quarter inch diameter drill bit. Around the open end of the cylindrical portion of the spacer there is a snap 23 which is designed to interact with the indent 20 of the next adjacent spacer when the spacers are combined to form the drill stop.

The spacer may be molded from a plastic such as polyethylene or polypropylene or could be made of metal. The plastic spacers are preferred because of cost and because the flexibility of the plastic material allows the tabs of one spacer to be readily snapped into the head of the bore of an adjacent spacer.

In use, the desired number of spacers are fitted together to limit the extent that the drill bit would extend beyond the spacers. The distance that the drill bit 13 extends beyond the end of the spacer is the limit of the depth of penetration of the drill bit. The spacers can all be of the same dimension or they can be varied dimensions depending on the accuracy of the drill penetration desire. For example, the distance "B" shown in FIG. 2 could be 5, 10, or 15 millimeters which would allow the drill depth to be varied by as little as 5 mm. When in use, the desired number of spacers are joined together and fitted into the chuck 12 of the drill and around the drill bit 13. The extent that the drill bit extends beyond the distal spacer will determine the depth that the drill will penetrate before the surface of the distal spacer contacts the surface through which the drill penetrates.

We claim:

1. A cranial drill stop comprising a plurality of spacers, each of said spacers having a body having a first end and a second end, said first end comprising a cylindrical portion having a bore extending therethrough, said second end comprising a flat disk adjacent said cylindrical portion and having a plurality of tabs affixed thereto and extending perpendicular from the face of said disk and arrange in a circumferential pattern around a bore centrally located in said disk and axially aligned with the bore in said cylindrical portion, the periphery of said disk defining a gripping flange having a diameter larger than the diameter of said cylindrical portion, each of said tabs having an indent positioned on an outer surface, a bead positioned around the interior diameter of said cylindrical portion, said indents in said tabs adapted to engage and retain a bead of another spacer when the spacers are fitted together to define a drill stop.

2. The drill stop of claim 1 comprising at least three spacers, the axial length of the cylindrical portion of at least one of said spacers being a different length than that of at least one of the other spacers.

* * * * *